United States Patent
Leder et al.

(10) Patent No.: US 7,202,333 B1
(45) Date of Patent: Apr. 10, 2007

(54) DNA ENCODING IGE RECEPTOR α-SUBUNIT OR FRAGMENT THEREOF

(75) Inventors: Philip Leder, Chestnut Hill, MA (US); Akira Shimizu, Kyoto (JP); Reuben Siraganian, Bethesda, MD (US); Philip Benfey, New York, NY (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 08/128,321

(22) Filed: Sep. 29, 1993

Related U.S. Application Data

(63) Continuation of application No. 07/870,789, filed on Apr. 16, 1992, now abandoned, which is a continuation of application No. 07/510,614, filed on Apr. 18, 1990, now abandoned, which is a continuation of application No. 07/127,214, filed on Dec. 1, 1987, now Pat. No. 4,962,035.

(51) Int. Cl.
*C07K 14/705* (2006.01)

(52) U.S. Cl. ..................................... 530/350; 435/69.1

(58) Field of Classification Search ................ 530/350, 530/387
See application file for complete search history.

(56) References Cited

OTHER PUBLICATIONS

Hempstead et al. *Journal of Immunology* (1979) 123(5):2283-2291.*
Conrad et al. "The interaction of human and rodent IgE with the human basophil IgE receptor," J. Immunology, vol. 130, No. 1, pp. 327-333 (1983).*
Metzger et al Fed. Proc 41 (1) p. 8-11 (1982).*
Goetze et al Biochem 20 p. 6341-49 (1981).*
Kochan et al. Nucl. Acid Res. 16(8) p. 3584 (1988).*
Shimizu et al. PNAS 85 p. 1907-11 (1988).*
Baniyash et al J. of Immunol 138(9) p. 2999-3004 (1987).*
Stedmanis Medical Dictionary , 24 edition (1982) Williams & Wilkins : p. 1207.*

* cited by examiner

*Primary Examiner*—John Ulm
(74) *Attorney, Agent, or Firm*—Clark & Elbing, LLP

(57) ABSTRACT

A cDNA sequence encoding the α-subunit of human mast cell IgE surface receptor or an IgE binding fragment thereof.

1 Claim, 6 Drawing Sheets

FIG. 4a

```
Rat    ACTTTTGAAGCCGTAGCTCACTGGTGCAGTTAGCACCTGAAGGCACAGGG
                 ||  |  ||||  ||||||  |  |||  |
Human  ..................AC-AGCACAGTAAGCACCAGGAGTCCATGAA 1                          10
                M  D  T           G  G  S  A  R  L  C  A  L  V
Rat    GCA-ATGGATACT------GGAGGATCTGCCCGGCTGTGCCTAGCATTAGT
       | | ||||| ||       ||  |||  ||||| |||| ||||  |||| |
Human  GAAGATGGCTCCTGCCATGGAATCCCCTACTCTACTGTGTGTAGCCTTACT
             (M) A  P  A  M  E  S  P  T  L (L)(C) V (A)(L) L 20                          30
       L  I  S  L  G  V  M  L  T  A  T  Q  K  S  V  V  S
Rat    GCTCATATCTCTGGGTGTCATGCTAACAGCCACTCAGAAATCTGTAGTGTC
       |  |||   |||  |||||||||||||||| |  |||||||||  || ||
Human  GTTCTTCGCTCCAGATGGCGTGTTAGCAGTCCCTCAGAAACCTAAGGTCTC
       F  F  A  P  D  G  V (L) A  V  P (Q)(K) P  K (V)(S)

40
       L  D  P  P  W  I  R  I  L  T  G  D  K  V  T  L  I
Rat    CTTGGACCCACCGTGGATTAGAATACTTACAGGAGATAAAGTGACTCTTAT
       ||||  ||||  || |||| ||||| ||||||| ||| ||||||||||| |
Human  CTTGAACCCTCCATGGAATAGAATATTTAAAGGAGAGAATGTGACTCTTAC
       (L) N (P)(P)(W) N (R)(I) F  K (G) E  N (V)(T)(L) T 50                          60
       C  N  G  N  N  S  S  Q  M  N  S  T  K  W  I  H  N
Rat    ATGCAATGGGAACAATTCCTCTCAAATGAACTCTACTAAATGGATCCACAA
       ||| ||||||||||||| ||  ||||| | |  ||||||| ||| |||||
Human  ATGTAATGGGAACAATTTCTTTGAAGTCAGTTCCACCAAATGGTTCCACAA
       (C)(N)(G)(N)(N) F  F  E  V  S (S)(T)(K)(W) F (H)(N)

70                          80
       D  S  I  S  N  V  K  S  S  H  W  V  I  V  S  A  T
Rat    TGATAGCATCTCTAATGTGAAATCGTCACATTGGGTCATTGTGAGTGCCAC
       || ||| ||  |  |||  |  |||  |||||  | ||||| || |||||
Human  TGGCAGCCTTTCAGAAGAGACAAATTCAAGTTTGAATATTGTGAATGCCAA
       G (S) L (S) E  E  T  N (S) S  L  N (I)(V) N (A) K 90
       I  Q  D  S  G  K  Y  I  C  Q  K  Q  G  F  Y  K  S
Rat    CATTCAAGACAGTGGAAAATACATATGTCAGAAGCAAGGATTTTATAAGAG
       | || |||||||||| | ||||| |||||| || ||| | |||  || ||
Human  ATTTGAAGACAGTGGAGAATACAAATGTCAGCACCAACAAGTTAATGAGAG
       F  E (D)(S)(G) E (Y) K (C)(Q) H (Q) Q  V  N  E (S)
```

FIG. 4b

```
         100                   110
     K   P   V   Y   L   N   V   M   Q   E   W   L   L   L   Q   S   S
Rat  CAAACCTGTGTACTTGAACGTGATGCAAGAGTGGCTGCTGCTCCAATCTTC
     |||||||||||| || | ||  |   || |||||||||| || ||  | ||
Human TGAACCTGTGTACCTGGAAGTCTTCAGTGACTGGCTGCTCCTTCAGGCCTC
     E  (P)(V)(Y)(L)  E  (V)  F   S   D  (W)(L)(L)(L)(Q)  A  (S)

120                   130
     A   D   V   V   L   D   N   G   S   F   D   I   R   C   R   S   W
Rat  TGCTGACGTGGTCTTAGACAATGGATCCTTTGACATCAGATGCCGTAGCTG
     ||||||  ||||| |  ||        ||| |    |||| |||| | |||
Human TGCTGAGGTGGTGATGGAGGGCCAGCCCCTCTTCCTCAGGTGCCATGGTTG
     (A)  E  (V)(V)  M   E   G   Q   P   L   F   L  (R)(C)  H   G  (W)

140                       150
     K   K   W   K   V   H   K   V   I   Y   Y   K   D   D   I   A   F
Rat  GAAGAAATGGAAAGTCCACAAGGTGATCTACTACAAGGACGACATTGCTTT
     ||  ||| ||| | ||  ||||||||||||| || ||||| |    ||| |
Human GAGGAACTGGGATGTGTACAAGGTGATCTATTATAAGGATGGTGAAGCTCT
     R   N  (W)  D  (V)  Y  (K)(V)(I)(Y)(Y)(K)(D)  G   E  (A)  L 160
     K   Y   S   Y   D   S   N   N   I   S   I   R   K   A   T   F   N
Rat  CAAGTACTCTTATGACAGCAACAACATCTCCATTAGAAAGGCCACATTTAA
     |||||||   |||| |||  ||||||||||||||| | |||||||| ||| |
Human CAAGTACTGGTATGAGAACCACAACATCTCCATTACAAATGCCACAGTTGA
     (K)(Y)  W  (Y)  E   N   H  (N)(I)(S)(I)  T   N  (A)(T)  V   E 170                    180
     D   S   G   S   Y   H   C   T   G   Y   L   N   K   V   E   C   K
Rat  TGACAGTGGCAGCTACCACTGCACAGGCTATTTGAACAAGGTTGAATGTAA
     ||||||| ||| | || ||||| |||| || ||  ||  || | ||| ||
Human AGACAGTGGAACCTACTACTGTACGGGCAAAGTGTGGCAGCTGGACTATGA
     (D)(S)(G)  T  (Y)  Y  (C)(T)(G)  K   V   W   Q   L   D   Y   E 190                   200
                                                           I   T   Q   L   S   I   V
     S   D   K   F   S   I   A   V   V   K   D   Y   T   I   E   Y   R
Rat  ATCTGATAAATTCAGTATTGCTGTAGTAAAAGATTACACAATTGAGTATCG
     ||||| |  | || ||||| |||| || ||||  |     |||| | |
Human GTCTGAGCCCCTCAACATTACTGTAATAAAAGCT---CCGCGTGAGAAGTA
     (S)  E   P   L   N  (I)  T  (V)  I  (K)  A   -   P   R  (E)  K   Y
```

FIG. 4c

```
                       210
          G  Y  N  S  F  S  H  H  W  R  *
          W  L  Q  L  I  F  P  S  L  A  V  I  L  F  A  V  D
Rat       TTGGCTACAACTCATTTTCCCATCATTGGCGGTGATTCTGTTTGCTGTGGA
          |||||||||| |  || ||||||  ||||  |||||||||||||||||||
Human     CTGGCTACAATTTTTTATCCCATTGTTGGTGGTGATTCTGTTTGCTGTGGA
         (W)(L)(Q)  F  F  I (P) L (L) V (V)(I)(L)(F)(A)(V)(D)

220                    230
          T  G  L  W  F  S  T  H  K  Q  F  E  S  I  L  K  I
Rat       CACTGGGTTATGGTTCTCAACCCACAAACAGTTCGAATCCATCTTGAAGAT
          ||| || ||||   |||||||| ||  || ||  |  |||| ||||||||
Human     CACAGGATTATTTATCTCAACTCAGCAGCAGGTCACATTTCTCTTGAAGAT
         (T)(G)(L) F  I (S)(T) Q  Q (Q) V  T  F  L (L)(K)(I)

240
          Q  K  T  G  K  G  K  K  K  G  *
Rat       TCAGAAGACTGGAAAAGGCAAAAAAAAAGGTTGAAACCTAACTCTTAACCA
          | |||  || |  |||||||        ||   ||||  |  || ||||
Human     TAAGAGAACCAGGAAAGGC---TTCAGACTTCTGAACCCACATCCTAAGCCA
          K  R (T) R (K)(G)    F  R  L  L  N  P  H  P  K  P Rat       AGGTATATAAAGGAACTAATGTCATCGCTTAAGAGACAATTCTTAACAATT
          |   |  ||| ||| | |  ||  ||   || ||| ||| ||| || |||
Human     AACCCCA-AAAACAACTGATATAATTACTCAAGA-AATATTTGCAAC-ATT
          N  P  K  N  N  *

Rat       A--TTTCCCACAGTATCTTCAATAGCCTTTCAACTGTCAAAGGACA-CTCA
          |  |||   |||  |||  ||||| ||  ||||||||||  |||| ||||
Human     AGTTTTTTTCCAGCATCAGCAATTGCTACTCAATTGTCAAA-CACAGCTTG Rat       TGTTATCCATAGAAATGTCTGTACCCCAGGAATTGCATAAATGCTTCATTA
          ||| |||||||||| |||||| ||||   |   |||  ||||||||||||
Human     CAATATACATAGAAACGTCTGTGCTCAAGGATTTATAGAAATGCTTCATTA Rat       AACCAACAGCAGCTGGTTAAGTGACATGCAATAAATAACAAATACTCAATA
          |||  |  |  ||||||||||||  ||||     |||| || ||||||||
Human     AACTGAGTGAAACTGGTTAAGTGGCATG----TAATAGTAAGTGCTCAATT Rat       AACACTGGTTTAAGAAGTTAAAGAATGAGCTGATTGCTTTGTCTATATCTG
          |||| |||||| || || | | ||||||||  |||| ||| |   || ||
Human     AACATTGGTTGAATAAATGAGAGAATGAATAGATTCATTTATTAGCATTTG
```

FIG. 4d

```
Rat       TAAAAGAGAAGTACAATTTGAATAAAGTATGGAATCATGTAGAATGGTAAA
          ||||||||||  || ||||||| ||||||| ||    |||  ||   ||||
Human     TAAAAGAGATGTTCAATTTCAATAAAATA---AAT-ATAAAACCATGTAAA Rat       AAAA(polyA)
          ||||
Human     AAAA(polyA)
```

DNA ENCODING IGE RECEPTOR α-SUBUNIT OR FRAGMENT THEREOF

This is a continuation of application Ser. No. 07/870,789, filed Apr. 16, 1992, now abandoned, which is a continuation of application Ser. No. 07/510,614 filed on Apr. 18, 1990, now abandoned, which is a continuation of application Ser. No. 07/127,214 filed on Dec. 1, 1987, now U.S. Pat. No. 4,962,035 issued on Oct. 9, 1990 by Philip Leder, Akira Shimizu, Rueben Siraganian, and Philip Bersey for DNA ENCODING IGE RECEPTOR ALPHA-SUBUNIT OR FRAGMENT THEREOF.

BACKGROUND OF THE INVENTION

Mast cells, which are located in the connective tissue of higher vertebrates, store histamine, prostaglandins (local chemical mediators), and proteases within cytoplasmic granules. When stimulated (e.g., by immunological reaction), the contents of these granules are released from the mast cell. Histamine acts only on cells in its immediate vicinity and, upon release, causes blood vessels to dialate, thereby increasing their permiability to serum proteins (e.g., antibodies) and other immune system components (e.g., leukocytes). Histamine is largely responsible for the clinical symptoms of "allergic reactions" such as hay fever (Metzger et al., 1986, Ann. Rev. Immunol. 4:419).

Immunological stimulation is mediated by IgE molecules, IgE being one of the five classes of antibodies found in higher vertebrates. IgE molecules bind with high affinity to an abundant, specific mast cell surface receptor. Bound IgE molecules, in turn, bind specific allergen molecules and considerable evidence indicates that the trigger for the release of the mast cell cytoplasmic granule contents is the allergen mediated cross-linking of two or more bound IgE molecule (Metzger et al., 1986, Ann. Rev. Immunol. 4:419; Ishizaka et al., 1977, J. Immunol. 119: 1589; Isersky et al., 1978, J. Immunol. 121:549; Froese, 1984, Prog. Allergy 34:142; Lewis and Austen, 1981, Nature 293:103).

The mast cell surface receptor consists of three subunits, a heavily glycosylated α-subunit of 50–60 kd exposed to the outer surface of the cell and bearing the IgE-binding site, and two non-glycosylated intramembrane components, the β and γ subunits, of approximately 30 and 20 kd, respectively (Metzer et al, 1986, Ann. Rev. Immunol. 4:419; Froese, 1984, Prog. Allergy 34:142).

SUMMARY OF THE INVENTION

In general, the invention features a cDNA sequence encoding the α-subunit of human mast cell IgE surface receptor.

The invention also features a vector (plasmid or viral) containing DNA encoding the α-subunit of human mast cell IgE surface receptor.

The invention additionally features a soluble fragment of the α-subunit of human mast cell IgE surface receptor, such fragment being capable of binding to human IgE.

The human IgE receptor α-subunit, or fragments thereof, made according to the invention can be used in a variety of diagnostic and therapeutic applications, as will be explained in more detail below.

Other features and advantages of the invention will be apparent from the following description of the preferred embodiments, and from the claims.

DESCRIPTION OF THE PREFERRED EMBODIMENTS

The drawings will first be described.

DRAWINGS

FIG. 4 is a diagrammatic comparison of the DNA sequences of rat and human IgE receptor α-subunit cDNA clones.

The cDNA sequence encoding human mast cell IgE surface receptor α-subunit was produced according to the following general series of steps. First, rat IgE surface receptor α-subunit was purified, fragmented, and tryptic peptides produced. A rat cDNA clone was then isolated using oligonucleotides designed on the basis of the amino acid sequence of one of the tryptic peptides. A human cDNA library was then prepared, and the rat cDNA fragments were used to screen the human library. In more detail, these procedures were carried out as follows.

Rat IgE Receptor Protein Purification, Tryptic Peptide Preparation, and Sequence Determination Rat basophilic leukemia (RBL-2H3) cells were solubilized and incubated overnight at 4° C. with monoclonal anti-rat mast cell IgE receptor antibody (mAb BC4) coupled to Sepharose 4B beads (Basciano et al., 1986, J.B.C., Vol. 261, page 11823). The beads were washed and the bound proteins were eluted with 5% acetic acid and then lyophilized. Aliquots were analyzed by $NaDodSO_4$-PAGE (Laemmli, 1970, Nature 227:680) followed by silver staining (Oakley et al., 1980, Anal. Biochem. 105:361). As expected, there were bands corresponding to α, β, and γ chains of the receptor. The different receptor components were further purified by elution from $NaDodSO_4$-PAGE.

Figure 1:
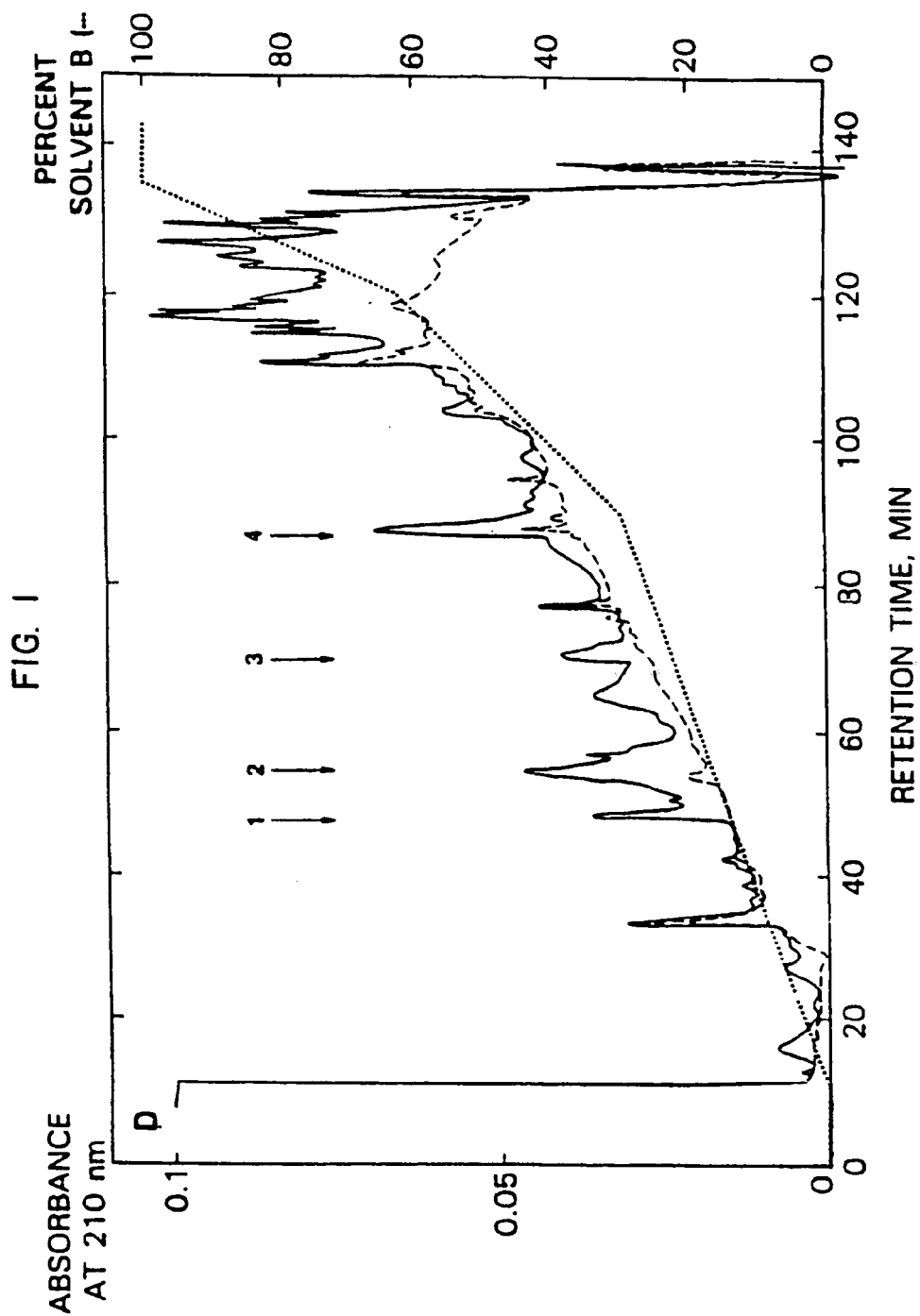
FIG. 1 is the HPLC elution profile of rat IgE surface receptor α-subunit tryptic digest fragments.

Amino acid sequence determination by N-terminal analysis was inappropriate because the N-terminal end of the eluted α-subunit samples appeared to be blocked. The samples therefore were reduced with 2 mM dithiothreitol in 6M guanidine HCl, 100 mM Tris (pH 8.3) and 1.0 mM EDTA at 37° C. under $N_2$ and were then S-carboxymethylated with 10 mM iodoacetic acid. Salts were removed by HPLC on a Vydac $C_4$ column. Desalted samples were treated with TPCK (L-1-tosylamido-2-phenylethyl chloromethyl ketone) treated trypsin in 100 mM Tris (pH 7.2). The resulting tryptic peptides were separated by HPLC on a Vydac $C_4$ column; the elution profile is shown in FIG. 1. Peaks indicated by arrows were subjected to amino acid sequencing using an Applied Biosystems vapor phase amino acid sequencer. Peptide sequences obtained from these peaks are shown in Table 1, below.

TABLE 1

| | |
|---|---|
| WIHNDSISNXK and YSYDSNXISIR | (Peak 1) |
| ILTGDKVTLIXNG | (Peak 2) |
| VIYYK | (Peak 3) |
| SVVSLDPPWIR | (Peak 4) |

Isolation of Rat Mast Cell IgE Receptor α-Subunit cDNA Clones and Nucleotide Sequence Determination The strategy for isolating rat IgE receptor α-subunit cDNA was to synthesize oligonucleotides predicted to be complementary to the rat α-subunit gene, and then use those oligonucleotides to screen a rat cDNA library.

Oligonucleotide Probes

Computer assisted analysis of the tryptic fragments was carried out using software versions 4 and 5 from the Genetics Computer Group of the University of Wisconsin (Devereux et al., Nucl. Acids Res. 12:7035). Among the peptide sequences, peptide 4 (FIG. 1, peak 4) showed significant homology to a sequence near the $NH_2$-terminus of the mouse Fcγ (IgG) receptor (Ravetch et al., 1986, Science 234:718), suggesting an analogous sequence in the IgE receptor subunit. From the sequence of peptide 4, the least codon-redundant portion, Asp-Pro-Pro-Trp-Ile, was chosen to make a 32-mixture of the 14mer oligonucleotide, 5'-ATCCA(A/G/C/T)GG(A/G/C/T) GG(A/G)TC-3' using an automated DNA synthesizer (Models 380A and B, Applied Biosystems). The oligonucleotides were labeled using $^{32}P$ as described in Maniatis et al. (1982), *Molecular Cloning*.

Construction and Screening of cDNA Libraries

RNAs were extracted from rat RBL-2H3 cells by homogenizing in 6M guanidinium isothiocyanate followed by ultracentrifugation over a CsCl cushion as described in Maniatis et al. (1982) *Molecular Cloning*, followed by phenol-chloroform-isoamyl alcohol (25:24:1) extraction. Poly(A)+ RNAs were prepared using oligo(dT) cellullose columns (Aviv and Leder, 1972, Proc. Natl. Acad. Sci. U.S.A. 69:1408), and cDNA libraries were constructed as described in Okayama and Berg, 1983, Molec. Cell. Biol. 3:280 using slightly modified vector and linker fragments (Noma et al., 1986, Nature 319:640). From 5 μg of poly (A)+ RNA, $9 \times 10^5$ independent colonies were obtained.

About $7 \times 10^4$ independent colonies were screened with labelled oligonucleotide probe, by the method described in Hahahan and Meselson, 1980, Gene 10:63, and three positive clones were identified. The nucleotide sequences of two of the three clones which showed similar restriction enzyme digestion patterns were determined by the dideoxy chain termination method described in Sanger et al., 1977, Proc. Natl. Acad. Sci. U.S.A. 74:5463 using alkali-denatured plasmid DNA.

Figure 2:
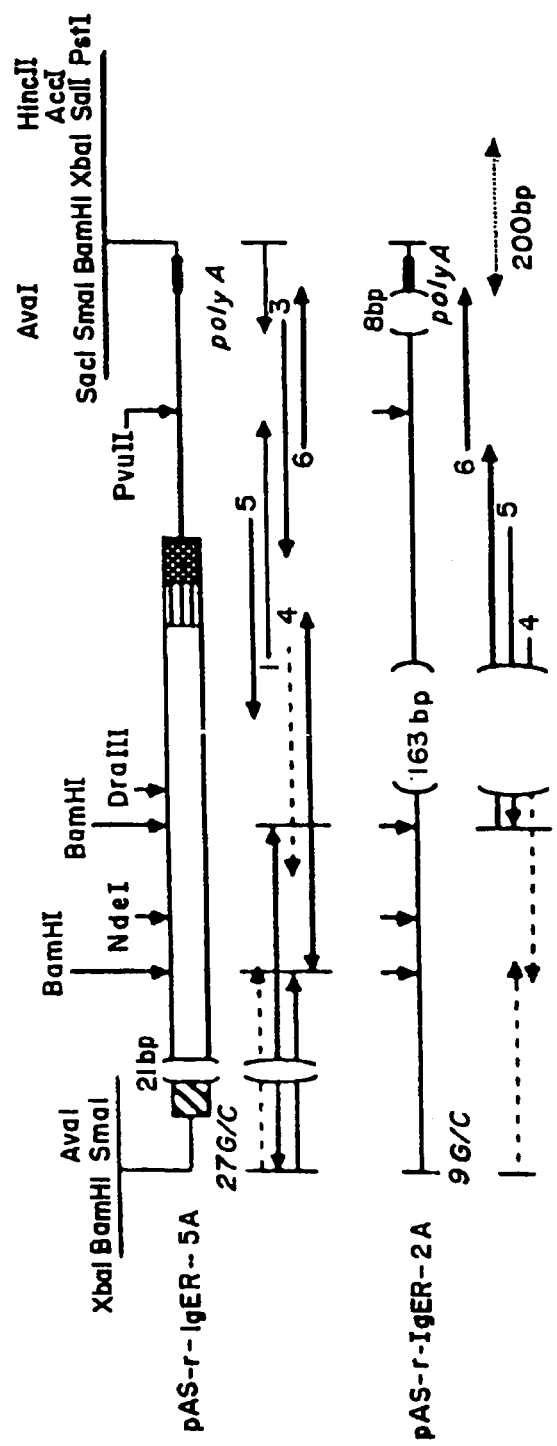
FIG. 2 is a pair of restriction maps of two rat IgE receptor α-subunit clones.
Figure 3:
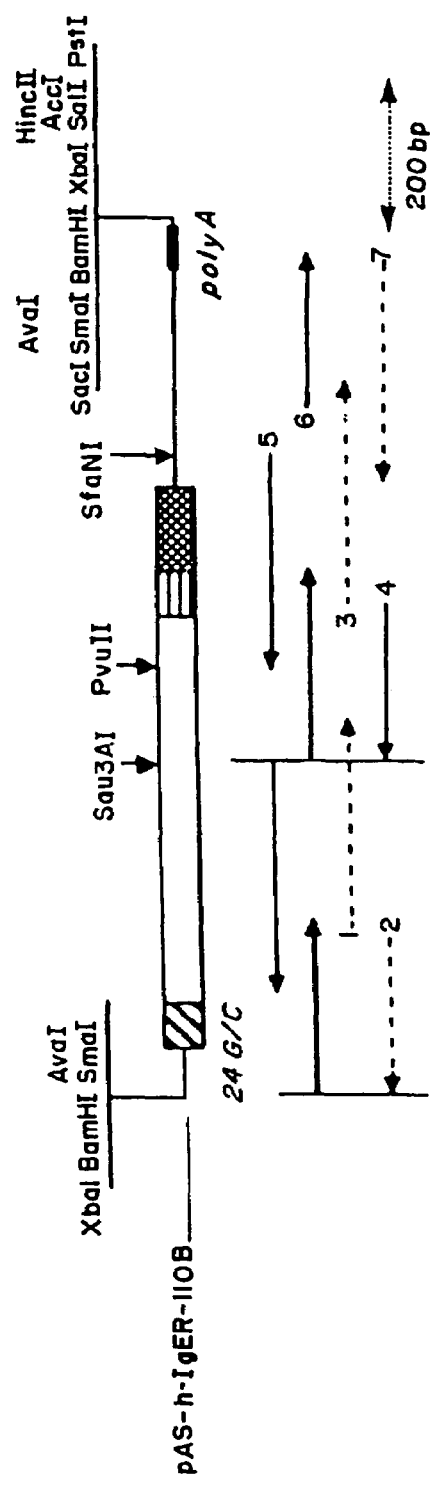
FIG. 3 is a restriction map of a human IgE receptor α-subunit clone.

Referring to FIGS. 2 and 4, respectively, these clones have exactly the same sequence except for one deletion (bp 21) in pAS-r-IgER-5A (cl 5A) and two deletions (bp 163 and 8) in pAS-r-IgER-2A (cl 2A). A full length cDNA clone (cl 2A/5A) was constructed by combining the left one-third of the cl 2A cDNA with the right two-thirds of the cl 5A cDNA. In RNase protection experiments (Melton et al., 1984, Nucl. Acids Res. 12:7035) using a labelled RNA transcribed from the clone 2A/5A cDNA in pGEM3, a plasmid containing the promoter sequence for T7 RNA polymerase, the majority of the IgE receptor mRNA was shown to have no deletions. This observation permitted the primary structure of rat IgE receptor α-subunit to be deduced from the 735 bp open reading frame of the undeleted sequence (FIG. 4). That open reading frame was found to encode a 245 amino acid peptide containing perfect-matches to the peptide sequences which had been determined by amino acid sequencing.

Isolation of the Human Mast Cell IgE Receptor α-Subunit cDNA Clone

To clone the human α-chain cDNA, a cDNA library was prepared, generally as outlined above, from a human mast cell line known to produce IgE receptors (KU812). About $9 \times 10^4$ colonies were screened with nick-translated HpaII (46)-PvuII(970) fragment of rat cDNA clone 2A/5A. Hybridization was carried out in 6× SSC −50% formamide −10% dextran sulfate at 42° C., 15 hours, and the filters were then washed twice in 0.1× SSC and 0.1% $NaDodSO_4$ at 55° C. for 15 minutes. Three positive colonies were identified, and the one which had the largest insert (pAS-h-IgER-110B) was further characterized. Both nucleotide and deduced amino acid sequences were compared with the rat sequence (FIG. 4).

Insertion into an Expression Vector

The human cDNA sequence of the invention can be inserted, by conventional techniques, into any of a variety of expression vectors to produce recombinant human mast cell IgE receptor α-subunit of the invention. Shortened sequences can be used for the production of soluble fragments.

The cDNA encoding the human mast cell IgE surface receptor α-subunit can, for example, be inserted into the expression vector described in Ringold U.S. Pat. No. 4,656,134, hereby incorporated by reference. This plasmid can then be used to transform mammalian host cells, and the human mast cell IgE receptor α-subunit can be isolated and purified according to conventional methods.

In its unglycosylated form, the polypeptide can be produced in a bacterial host, e.g., *E. coli*. The cDNA encoding the human mast cell IgE surface receptor α-subunit can, for example, be inserted into the expression vector described in DeBoer et al., 1983, Proc. Natl. Acad. Sci. 80:21. The plasmid, which carries the hybrid tac promoter, can be used to transform *E. coli*, and the α-subunit can be isolated and purified according to conventional methods.

Use

The human mast cell IgE surface receptor α-subunit of the invention, or a fragment thereof, can be used to produce anti-IgE surface receptor polyclonal or monoclonal antibodies using conventional methods. These antibodies can be used in an in vitro diagnostic assay, of any standard format, e.g., ELISA, to determine the level of IgE receptor in a biological sample obtained from a human patient, e.g., blood or tissue samples, in particular, in basophils. The amount of IgE receptor α-subunit present in the sample can serve as a measure of the allergic response of the patient to a substance to which the patient has been exposed. IgE receptor α-subunit levels can also be measured to determine the efficiency of anti-allergy therapies, and to monitor a patient's allergic status over time. The antibodies can also be used in the immunochromatographic purification of IgE receptor α-subunit from culture media.

The IgE receptor α-subunit, or soluble fragments thereof, can also be used therapeutically to treat human patients suffering from allergies. The IgE receptor α-subunit or fragment thereof competes for IgE with the receptor naturally present on mast cells, so that IgE is bound to the administered peptide and unable to bind to mast cells to mediate the allergic response. As an alternative to using the peptide itself in competitive inhibition therapy, the peptide can be used to design non-peptide drugs which behave therapeutically like the peptides. Generally, X-ray crystallography is used to elucidate the three-dimensional structure of the peptide, in particular its IgE binding sites, and a non-peptide compound is synthesized, with the aid of computer modelling, to mimic the functionally important regions of the peptide.

The peptide, or compound synthesized on the basis of the structure of the peptide, will be administered as an unmodified peptide or in the form of a pharmaceutically acceptable salt, admixed with a physiologically acceptable carrier, e.g., saline. Examples of preferred salts are those of therapeutically acceptable organic acids, e.g., acetic, lactic, maleic, citric, malic ascorbic, succinic, benzoic, salicylic, methanesulfonic, toluenesulfonic, or pamoic acid, as well as polymeric acids such as tannic acid or carboxymethyl cellulose, and salts with inorganic acids such as hydrohalic acids, e.g., hydrochloric acid, sulfuric acid, or phosphoric acid. The composition can be in the form of a liquid, for intravenous, subcutaneous, parenteral, or intraperitoneal administration, or a spray for bronchial or nasal administration.

The IgE receptor α-subunit can also be used to screen substances which potentially have the capacity to bind to the IgE receptor α-subunit; such substances, when administered therapeutically to a human patient suffering from an allergy, can alleviate the allergic response by binding to the IgE receptor α-subunit on the patient's mast cells, thus preventing IgE from binding and thereby interrupting the IgE-mediated allergic response. Screening for such IgE receptor α-subunit binding substances can be carried out by immobilizing the α-subunit, bringing the substance to be screened, in labeled form (e.g., radiolabeled), into contact with the immobilized subunit, separating soluble from immobilized phases, and detecting bound label as an indication of binding.

Deposit

The cDNA vectors encoding the human and rat IgE receptor α-subunits were deposited in the American Type Culture Collection, 12301 Parklawn Drive, Rockville, Md., on Dec. 1, 1987, and were given ATCC Accession Nos. 67566 (human α-subunit; *E. coli* pGEM-3-110B-1) and 67567 (rat α-subunit; *E. coli* pGEM-32A/5A-1). One of applicants' assignees, President and Fellows of Harvard College, hereby acknowledge their responsibility to replace this culture should it die before the end of the term of a patent issued hereon, 5 years after the last request for a culture, or 30 years, whichever is the longer, and their responsibility to notify the depository of the issuance of such a patent, at which time the deposit will be made irrevocably available to the public. Until that time the deposit will be made available to the Commissioner of Patents under the terms of 37 CFR Section 1–14 and 35 USC Section 112.

OTHER EMBODIMENTS

Other embodiments are within the following claims. For example, the soluble α-subunit fragment of the invention need not have perfect homology with the corresponding region of the naturally-occurring molecule, but need only have sufficient homology (generally, at least 75%) to bind to human IgE. The fragment also must be large enough (generally, at least ten amino acids) to bind IgE. If solubility is desired, the fragment preferably should contain none of the hydrophobic transmembrane portion of the naturally occurring molecule. Fragments of the α-subunit, as well as the whole molecule, can be used to raise antibodies, useful as described above for diagnostic and purification purposes.

What is claimed is:

1. A recombinant soluble fragment of the α-subunit polypeptide of human mast cell IgE surface receptor, said fragment being capable of binding to human IgE.

* * * * *